United States Patent [19]

Van Der Plank

[11] Patent Number: 4,968,791

[45] Date of Patent: Nov. 6, 1990

[54] PROCESS FOR THE PREPARATION OF POLYOL FATTY ACID ESTERS

[75] Inventor: Pleun Van Der Plank, De Lier, Netherlands

[73] Assignee: Lever Brothers Company, New York, N.Y.

[21] Appl. No.: 217,785

[22] Filed: Jul. 12, 1988

[30] Foreign Application Priority Data

Jul. 23, 1987 [EP] European Pat. Off. ........ 87201425.3

[51] Int. Cl.$^5$ .................... C07H 1/00; C07H 15/00
[52] U.S. Cl. ................... 536/119; 536/124; 536/115; 536/116; 536/120
[58] Field of Search ............ 536/119, 124, 115, 116, 536/120

[56] References Cited

U.S. PATENT DOCUMENTS

| | | | |
|---|---|---|---|
| 3,792,041 | 10/1970 | Yamagishi et al. | 536/119 |
| 3,963,699 | 6/1976 | Rizzi et al. | 536/119 |
| 4,517,360 | 5/1985 | Volpenhein | 536/119 |
| 4,518,772 | 5/1985 | Volpenhein | 536/119 |
| 4,797,300 | 1/1989 | Jandacek et al. | 426/549 |
| 4,822,875 | 4/1989 | McCoy et al. | 536/119 |

FOREIGN PATENT DOCUMENTS

EP 0311154 4/1989 European Pat. Off. .

*Primary Examiner*—Ronald W. Griffin
*Assistant Examiner*—Everett White
*Attorney, Agent, or Firm*—Gerard J. McGowan, Jr.

[57] ABSTRACT

The present invention relates to a process for the preparation of polyol fatty acid esters, in which fatty acid esters are reacted with a polyol having at least 4 hydroxyl groups, or an ester thereof, wherein the fatty acid soap comprises at least 75% of a short-chain fatty acid soap, having a fatty acid chain length of less than 15 carbon atoms. Further the invention relates to the use of the polyol fatty acid esters thus prepared in foodstuffs, pharmaceutical compositions, detergents and coating compositions.

8 Claims, No Drawings

PROCESS FOR THE PREPARATION OF POLYOL FATTY ACID ESTERS

BACKGROUND OF THE INVENTION

The present invention relates to a process for the preparation of polyol fatty acid esters, in which fatty acid esters are reacted with a polyol having at least 4 hydroxyl groups, or an ester thereof, in the presence of fatty acid soap and a catalyst.

In a further aspect the invention relates to the use of the polyol fatty acid esters thus prepared in foodstuffs, pharmaceutical compositions, detergents and coating compositions.

In this specification by "polyol, having at least 4 hydroxyl groups" is meant any aliphatic or aromatic compound comprising at least 4 hydroxyl groups, and by "an ester thereof" is meant any partial fatty acid esters of such a polyol, which are intermediates in the conversion of polyol to higher polyol fatty acid esters.

The aforementioned process is known in the art. It is described in U.S. Pat. No. 3,963,699 (G. P. Rizzi & H. M. Taylor), U.S. Pat. No. 4,517,360 (R. A. Volpenhein), U.S. Pat. No. 4,518,772 (R. A. Volpenhein) and J. Am. Oil Chem. Soc. 55 (1978), 398–401 (G. P. Rizzi & H. M. Taylor), U.S. Pat. No. 3,792,041 (Yamagishi et al.).

A drawback of the conventional processes is that the conversion rate of polyol to polyol fatty acid ester is relatively low. In particular, when carrying out these processes batchwise, it takes a rather long time before a desired conversion is reached, during which time the reaction vessel will not be available for a subsequent batch.

SUMMARY OF THE INVENTION

Surprisingly, it has now been found that the conversion rates of polyol to polyol fatty acid esters are increased if the soap component comprises a certain level of short-chain fatty acid soaps.

Accordingly, the present invention provides a process for the preparation of polyol fatty acid esters, in which fatty acid esters are reacted with a polyol having at least 4 hydroxyl groups, or an ester thereof, in the presence of fatty acid soap and a catalyst, characterized in that said fatty acid soap comprises at least 8% by weight of short-chain fatty acid soap having a fatty acid chain length of less than 15 carbon atoms.

Due to the high conversion rate it is possible to use the means of production of polyol fatty acid esters more efficiently allowing a more cost-effective operation thereof.

Yet another advantage of the process according to the invention is the fact that the application of short chain fatty acid soap results in a relatively low viscosity for the reaction mixture during the process. Thus it is possible to mix the components more intimately. Moreover it takes less energy to obtain the same grade of homogenization when using short-chain fatty acid soap, than it would have taken if longer chain fatty acid soaps were used.

A further advantage of the process according to the present invention is that relatively little foaming occurs during the process, which allows better process control.

The fatty acid soap suitable for use in the process of the present invention can be both saturated and unsaturated. Preferably alkali metal or alkaline earth metal soaps are used. Best results are obtained when alkali metal soaps, such as sodium and preferably potassium soaps, are used.

An essential feature of the present invention is that the fatty acid soap comprises at least 8% by weight of fatty acid soap having a fatty acid chain length of less than 15 carbon atoms. Preferably, the fatty acid soap comprises at least 15% by weight of the short-chain fatty acid soap. Even higher conversion rates are obtained when using a soap containing at least 75% by weight of the short chain fatty acid soap.

Normally the soap concentration in the reaction medium of the process according to the invention ranges from 1 to 15% by weight, and preferably, from 2 to 12 by weight of the total reaction mixture.

The molar ratio, in the reaction mixture, of soap to polyol is preferably at least 0.1:1, in particular, at least 0.5:1. Good results are obtained if the molar-ratio is less than 2.5:1.

Particularly good results are obtained if the molar ratio of short-chain fatty acid soap to polyol ranges from 0.2 to 1.6.

Although a substantial benificial effect is obtained from using short-chain fatty acid soaps having a chain length of less than 15 carbon atoms, it is preferred to use short-chain fatty acid soaps having a chain length ranging from 6 to 12 carbon atoms. Best results are obtained by using short-chain fatty acid soaps having a chain length ranging from 10 to 12 carbon atoms.

DETAILED DESCRIPTION OF THE INVENTION

Polyols which may suitably be interesterified using the process according to the present invention are defined in a general chemical sense hereinbefore. More specifically, they may be straight and branched chain linear aliphatics, saturated and unsaturated cyclic aliphatics including heterocyclic aliphatics, or mononuclear and polynuclear aromatics, including heterocyclic aromatics, having at least 4 hydroxyl groups.

As the polyol fatty acid esters prepared by a process according to the present invention are preferably used in food products and pharmaceutical compositions, preferably non-toxic polyols are used in the process. Accordingly, it is preferred to apply the process to the interesterification of sugar polyols, such as monosaccharides, oligosaccharides, polysaccharides and sugar alcohols. Also sugar-derivatives may be used successfully, e.g. alpha-methyl glucoside (alpha methyl ether of glucose).

Examples of monosaccharides which be used are glucose, mannose, galactose, arabinose, xylose, ribose, apiose, rhamnose, psicose, fructose, sorbose, tagitose, ribulose, xylulose, and reythrulose.

Examples of suitable oligosaccharides are maltose, kojibiose, nigerose, cellobiose, lactose, melibiose, gentiobiose, turanose, rutinose, trehalose, sucrose and raffinose.

Suitable polysaccharides are for example amylose, glycogen, cellulose, chitin, inulin, agarose, zylans, mannan and galactans.

Suitable sugar alcohols are erythritol, mannitol, sorbitol, xylitol and galactitol.

Preferred carbohydrates and sugar alcohols, suitable for use in the process according to the invention are xylitol, sorbitol and sucrose, the latter being preferred most.

Suitable fatty acid esters for use in the process of the present invention are esters of lower alcohols including mono-, di-, and triols. In particular, esters derived from $C_1$-$C_5$ alcohols are suitable, methanol being preferred.

The fatty acid residues in said fatty acid esters may be both saturated and unsaturated fatty acid residues having a chain length of 8 or more carbon atoms. Preferably the chain length of the fatty acid residues is less than 22 carbon atoms.

The amount of fatty acid ester depends on the desired degree of conversion, i.e. the percentage of polyol hydroxyl groups of the polyol fatty acid ester that on an average have been esterified with fatty acids. In particular, if high degrees of conversion or even full conversion is aimed at, in general excess amounts of fatty acid ester are used. For instance, in the synthesis of 100% converted sucrose good results are obtained when a molar ratio of fatty acid ester : sucrose is used within the range of from 10:1 to 20:1.

Suitable transesterification catalysts include the group consisting of alkali metals and alkaline earth metals, and their alkoxides, bicarbonates, carbonates, hydrides, hydroxides, and their alloys. KOH has been found to be particularly suitable, but also NaOH and the corresponding carbonates, and bicarbonates of potassium or sodium can be advantageously used. Although one might argue that the above reagents are not the catalysts themselves, but are reagents forming the catalyst, in this specification as is done in the literature relating to similar processes, this group will be referred to as catalysts.

The catalyst is used in an amount corresponding to a molar ratio of catalyst : polyol of at least 0.01:1, preferably of 0.05:1 to 1:1.

Separation of the polyol fatty acid esters from the other reaction products and starting materials can be achieved by using techniques known per se, for example by using organic solvents, water, or by salting out, e.g. according to the process described in U.S. Pat. No. 4,334,061.

In the process according to the invention soap may be added as such, but it is also possible to add a soap-precursor, which is converted into the corresponding soap in situ, for example by partial saponification of the fatty acid esters, or by neutralization of fatty acids. Preferably in such a case, there is used a solvent in which the alkaline substance used for saponification or neutralization is at least partially soluble so as to improve the saponification or neutralization.

Suitable solvents include water and lower alcohols, preferably $C_1$-$C_5$ alcohols, in particular methanol. When a solvent is used, it is recommendable to remove the solvent, e.g. by evaporation, before the resulting mixture, containing fatty acid esters and soap, is contacted with the catalyst and polyol.

A preferred embodiment of the present invention comprises the following steps: (1) polyol, or an ester thereof, is mixed with the alkaline catalyst in a liquid system in which system the alkaline catalyst can react with the polyol, or an ester thereof, forming a polyol anion; and (2) this liquid system is combined with the fatty acid ester.

The soap may be present in the liquid system of step (1), but can also be added separately, or together with the fatty acid ester, to the reaction mixture. In order to improve the contact between catalyst and polyol, or an ester thereof, in step (1) a solvent may be added. Suitable solvents include lower alcohols and/or ketones, of which the $C_1$-$C_5$ alcohols and ketones are preferred, and also water. When potassium or sodium hydroxide is used as a catalyst in the present process, water is a very suitable solvent, especially when these catalysts are used in combination with sucrose.

Step (1) may be carried out successfully at atmospheric pressure and room temperature. It is, however, also possible to carry out this step at other temperatures, e.g. 10°–80° C., or to apply a pressure higher or lower than atmospheric.

In principle, many types of alkali-resistant emulsifiers can be used to improve the contact of the ingredients in the reaction to be carried out in step (2). Known edible emulsifiers include mono/diglycerides, phosphatides such as lecithin, and detergents such as soaps, sodium dodecyl sulphate and partial sugar esters of fatty acids.

The transesterification reaction is suitably carried out at a temperature which normally lies within the range of from 100° to 180° C. Preferably temperatures are applied within the range of from 110° to 160° C., the range of from 120° to 150° C. being preferred most.

Preferably the reaction is carried out under such conditions that the alcohols formed during the esterification reaction are removed, for example by carrying out the reaction under reduced pressure, in particular under a pressure of less than 50 mbar.

The process according to the invention is preferably used for the production of di- and higher fatty acid esters of polyols. Therefore the polyol fatty acid esters obtained by the process, preferably comprise at least 50% by weight of di- and/or higher polyol fatty acid esters.

In an even more preferred embodiment the process is applied for the production of polyol fatty acid esters having a degree of conversion of at least 50%, in particular, of more than 70%. The production of polyol fatty acid polyesters having still higher degrees of conversion, i.e. degrees of conversion of more than 85% or even over 95% being preferred most.

The lower, i.e., mono-, di- and tri-, fatty acid esters of polyols, preferably comprising from 4 to 8 hydroxyl groups, are especially suited for application as emulsifier in foodstuffs, detergents, and/or drying oil in paint and varnish.

The tetra- and higher fatty acid esters of polyols having from 4 to 8 hydroxyl groups, and in particular the polyol fatty acid polyesters having degrees of conversion of over 85% are very suitably applied as a fat-replacer in foodstuffs and pharmaceutical compositions.

The invention is now further illustrated by the following examples.

EXAMPLE I

Step 1a—Formation of a liquid system containing sucrose and alkaline catalyst: 25.4 g (74.3 mmol) sucrose and 1.05 g of 85% KOH (16 mmol) were dissolved in 25 ml water, at room temperature and atmospheric pressure.

Step 1b—Soap formation: a mixture comprising 314 g (1061 mmol) methyl esters of soybean oil fatty acids, and 20.8 g (121 mmol) Prifrac 2906 (Trademark) fatty acids, mainly consisting of $C_{10}$ fatty acids, was neutralized by means of an aqueous solution of 7.97 g, 85% KOH (121 mmol) by adding said solution under vacuum at a temperature of 60° C.

Step 2—Reaction: under vigorous stirring, at a temperature of 60° C. and a pressure of 3 mbar, the sucrose-containing alkaline solution of step 1a was added to the reaction product of step 1b. The conditions were maintained constant for a period of 30 minutes, after which the water content of the mixture was less than 0.04%. Subsequently the temperature was raised to 120° C., after which the reaction started, which could be deduced from the formation of methanol, which was collected in a cold trap. During the reaction nearly no foaming occurred.

The molar ratio of KOH:sucrose in step 1a was 0.215. The molar ratio of methyl ester:sucrose was 14.3. The amount of soap used was 7% by weight of the total reaction-mixture.

In this example, and also in the examples described below, after 2 hours the conversion was determined. Also the time period needed to obtain (almost) complete conversion was measured. The values obtained in examples I–V, and comparative example A, are presented in Table I.

After removal of the soap, using the method as described in U.S. Pat. No. 4,334,061, a hydroxy number of 2.0 was measured. After separation of the methylesters, by steaming, a hydroxy number of 3.0 was found. The hydroxy numbers obtained in examples I, II and IV are represented in Table II.

EXAMPLES II-V

These examples are identical to example I, except that instead of Prifrac 2906 (Trademark) an equimolar amount of another fatty acid composition (see Table I) was used. The composition of these fatty acid compositions are represented in Table IV.

COMPARATIVE EXAMPLE A

This example is identical to example I, except for the fact that an equimolar amount of Prifrac 2960 (see table IV), mainly consisting of C16 fatty acids, was used. The results for this example are also represented in Table I.

EXAMPLE VI

Example I was repeated with the exception that, instead of methyl-esters of soybean oil, methylesters of groundnut oil were used, and that an equimolar amount of Prifrac 2920 (see table IV) was used. The yields obtained are represented in Table III.

COMPARATIVE EXAMPLES B-E

These examples are identical to example VII, except that the fatty acid compositions used, essentially consisted of fatty acids having a chain length of 16 or more carbon atoms. The composition of the fatty acid mixtures applied, can be found in Table IV. The results obtained are represented in Table III.

EXAMPLE VII

Example II was repeated using only half the amount of soap (60 mmol). The yield obtained was as follows:
after 2 hours: 13%
after 5 hours: 98%

EXAMPLE VIII

Example I was repeated with the exception that:
(1) the process was scaled up by a factor 10, using 254 g sucrose and 3140 g of soybean oil fatty acid methyl esters;
(2) a potassium soap of 139 g (0.65 mol) Prifac 7901 (Trademark) fatty acid composition was used; and
(3) in the aqueous sucrose-solution 11.15% potassium carbonate is applied, instead of potassium hydroxide.
The following yield was obtained:
after 2 hours: 17%
after 5 hours: 100%

EXAMPLE IX

In reaction mixtures obtained after the esterification of sucrose with methyl esters of soybean oil (or groundnut oil) fatty acids, in the presence of KOH, the viscosity of the reaction-mixtures was measured at different shear rates, at 60° C., using different soap compositions. The results are represented in Table V.

The initial molar ratio of fatty acid methyl esters:sucrose was 14.3, of fatty acid methyl esters:soap was 8.8 and of catalyst:sucrose was 0.22.

TABLE I

| example | Soap type | Soap origin | Conversion (in %) 2 hours | final | (hours) |
|---|---|---|---|---|---|
| (II) | $C_{14}$ | Prifrac 2942 | 48 | 98 | (5) |
| (III) | $C_{12}/C_{14}$ | Prifac 7901 | 34 | 100 | (6) |
| (IV) | $C_{12}$ | Prifrac 2920 | 80 | 100 | (4) |
| (I) | $C_{10}$ | Prifrac 2906 | 81 | 98 | (6) |
| (V) | $C_8$ | Prifrac 2901 | 43 | 99 | (7) |
| (A) | $C_{16}$ | Prifrac 2960 | 17 | 92 | (10) |

TABLE II

| example | hydroxy – number after soap removal | after steaming |
|---|---|---|
| (I) | 2.0 | 3.0 |
| (II) | 4.0 | 7.5 |
| (IV) | 2.0 | 4.0 |

TABLE III

| example | soap type | soap origin | conversion (in %) after 2 hours | final | (hours) |
|---|---|---|---|---|---|
| (VI) | $C_{12}$ | Prifrac 2920 | 84 | 97 | (5) |
| (B) | $C_{16}/C_{18}$ | Pristerene 4911 | 13 | 95 | (10) |
| (C) | $C_{18}$ | Prifrac 2981 | 21 | 95 | (10) |
| (D) | $C_{18}$-1 | Priolene 6930 | 13 | 98 | (11) |
| (E) | $C_{22}$ | Prifrac 2989 | 39 | 98 | (9) |

TABLE IV

| Product (*) | Composition (in wt. %) C6 | C8 | C10 | C12 | C14 | C16 | C18 |
|---|---|---|---|---|---|---|---|
| Prifrac 2906 | — | 0.4 | 98.4 | 0.2 | 0.1 | 0.2 | 0.1 |
| Prifrac 2942 | — | — | — | 0.7 | 96.2 | 1.0 | 0.2 |
| Prifac 7901 | 0.1 | 5.8 | 5.4 | 47.2 | 21.3 | 10.6 | 9.2 |
| Prifrac 2920 | — | — | 0.9 | 94.9 | 3.7 | 0.1 | — |
| Prifrac 2901 | 0.6 | 96.4 | 1.1 | — | 0.2 | — | — |
| Prifrac 2960 | — | — | — | — | 0.7 | 91.3 | 6.6 |
| Prifrac 2981 | — | — | — | — | — | 1.5 | 97.7 (1) |
| Prifrac 2989 | — | — | — | — | — | 0.9 | 2.8 (2) |
| Priolene 6930 | — | — | — | 0.1 | 3.7 | 12.6 | 78.0 (3) |
| Pristerene 4911 | — | — | — | — | 1.4 | 43.9 | 50.6 (4) |

(*) ex Unichema (Tradename)
(1) $C_{18}$ = $C_{18}$(saturated)
(2) fatty acid composition comprises 5.7% $C_{20}$, 87.6% $C_{22}$ and 0.8% $C_{24}$ (saturated) fatty acids by weight.
(3) $C_{18}$ = 1.9 wt. % $C_{18}$ (sat); 92.8 wt. % $C_{18}$-1 and 5.3 wt. % $C_{18}$-2
(4) $C_{18}$ = $C_{18}$(saturated)

TABLE V

| Shear-rate (1/s) | Viscosity in milli-Pascal S.BO.90 | S.C14.100 | S.C10.98 | S.C12.97* |
|---|---|---|---|---|
| −0.9 | 22864 | — | — | — |
| 1.8 | 12751 | — | — | — |
| 3.5 | 6925 | — | — | — |
| 7.0 | 3957 | — | — | — |
| 14.1 | 2254 | 289 | — | 412 |
| 28.2 | 1305 | 213 | — | 282 |
| 56.3 | 705 | 158 | — | 206 |

TABLE V-continued

| Shear-rate | Viscosity in milli-Pascal | | | |
|---|---|---|---|---|
| (l/s) | S.BO.90 | S.C14.100 | S.C10.98 | S.C12.97* |
| 112.6 | 458 | 127 | 38.5 | 162 |
| 225.3 | 306 | 102 | 38.6 | 131 |
| 450.6 | 224 | — | — | — | wherein
S.BO.90 = reaction-mixture, after 90% conversion, containing potassium-soap of soybean oil fatty acids.
S.C14.100 = reaction-mixture, after 100% conversion, comtaining potassium-soap of a fatty acid composition almost completely consisting of $C_{14}$ fatty acids.
S.C10.98 = reaction-mixture, after 98% conversion, containing potassium-soap of a fatty acid composition almost completely consisting of $C_{10}$ fatty acids.
S.C12.97* = reaction-mixture, originally comprising methyl esters of groundnut oil fatty acids, instead of soybean oil fatty acids, after 97% conversion, containing potassium soap of a fatty acid composition, almost completely consisting of $C_{12}$ fatty acids.

- S.C14.100=reaction-mixture, after 100% conversion, containing potassium-soap of a fatty acid composition almost completely consisting of $C_{14}$ fatty acids.

What is claimed is:

1. A process for the preparation of polyol fatty acid esters, in which fatty acid esters are reacted with a polyol having at least 4 hydroxyl groups, or an ester thereof, in the presence of fatty acid soap and a catalyst, in which process said fatty acid soap comprises at least 75% by weight of a short-chain fatty acid soap having a fatty acid chain length of less than 15 carbon atoms.

2. A process according to claim 1 wherein said short-chain fatty acid soap has a chain length ranging from 6 to 12 carbon atoms.

3. The process according to claim 2 wherein said short-chain fatty acid soap has a chain length ranging from 10 to 12 carbon atoms.

4. The process according to claim 1 wherein the concentration of said fatty acid soap ranges from 1 to 15% by weight of the total reaction mixture.

5. The process according to claim 1 wherein the molar ratio of said fatty acid soap to said polyol is at least 0.1:1 and less than 2.5:1.

6. The process according to claim 1 wherein the molar ratio of said short-chain fatty acid soap to said polyol having at least 4 hydroxyl groups ranges from 0.2 to 1.6.

7. The process according to claim 1 wherein polyol fatty acid esters comprising at least 50% by weight of polyol fatty acid esters selected from the group consisting of di- and/or higher polyol fatty acid esters are produced.

8. The process according to claim 1 wherein polyol fatty acid esters having a degree of conversion of more than 85% are produced.

* * * * *